(12) United States Patent
Nakamura et al.

(10) Patent No.: US 7,566,304 B2
(45) Date of Patent: Jul. 28, 2009

(54) ULTRASOUND DIAGNOSTIC DEVICE

(75) Inventors: Yasuhiro Nakamura, Tsukui-gun (JP); Akiko Uchikawa, Machida (JP); Hisashi Akiyama, Yokohama (JP); Morio Nishigaki, Fujisawa (JP); Hidenori Yoshitomi, Yokohama (JP)

(73) Assignee: Panasonic Corporation, Osaka (JP)

( * ) Notice: Subject to any disclaimer, the term of this patent is extended or adjusted under 35 U.S.C. 154(b) by 49 days.

(21) Appl. No.: 10/556,277

(22) PCT Filed: Jun. 10, 2004

(86) PCT No.: PCT/JP2004/008483

§ 371 (c)(1),
(2), (4) Date: Nov. 14, 2005

(87) PCT Pub. No.: WO2004/110278

PCT Pub. Date: Dec. 23, 2004

(65) Prior Publication Data

US 2007/0010744 A1    Jan. 11, 2007

(30) Foreign Application Priority Data

Jun. 11, 2003    (JP) .............................. 2003-166803

(51) Int. Cl.
*A61B 8/00*    (2006.01)
(52) U.S. Cl. .................................... 600/437
(58) Field of Classification Search ................. 600/437, 600/443; 604/22, 118; 606/169
See application file for complete search history.

(56) References Cited

U.S. PATENT DOCUMENTS 4,910,456 A * 3/1990 Elms ........................ 324/142

(Continued)

FOREIGN PATENT DOCUMENTS

JP    3-261466    11/1991

(Continued)

OTHER PUBLICATIONS

Chinese Office Action of the corresponding Chinese Patent Application No. 200480016388.9, Dec. 28, 2007.

(Continued)

*Primary Examiner*—Eric F Winakur
*Assistant Examiner*—Michael T Rozanski
(74) *Attorney, Agent, or Firm*—Hamre, Schumann, Mueller & Larson, P.C.

(57) ABSTRACT

A small ultrasound diagnostic device is provided at a low cost that enables the appropriate control by a single power supply unit so as to give a predetermined transmission power to a driving waveform different for each mode without excess or deficiency and without affecting properties of the driving waveform. The ultrasound diagnostic device includes: an ultrasound generation unit (1) that transmits ultrasound; a waveform generation unit (2) that generates a single pulse or a burst pulse whose duty factor is variable in units of a time that is a period corresponding to a frequency outside a frequency band of the ultrasound generation unit (1) so as to drive the ultrasound generation unit (1); and a single power supply unit (3) that determines an amplitude of a driving waveform generated by the waveform generation unit (2). Thereby, an acoustic power of the transmitted ultrasound can be controlled without making the transmission amplitude variable.

2 Claims, 4 Drawing Sheets

U.S. PATENT DOCUMENTS

| | | |
|---|---|---|
| 5,509,413 A | 4/1996 | Akama et al. |
| 5,694,937 A | 12/1997 | Kamiyama |
| 6,432,055 B1 | 8/2002 | Carp et al. |
| 6,669,638 B1 * | 12/2003 | Miller et al. ................ 600/438 |

FOREIGN PATENT DOCUMENTS

| | | |
|---|---|---|
| JP | 07-067877 A | 3/1995 |
| JP | 7-155322 | 6/1995 |
| JP | 7-155324 | 6/1995 |
| JP | 8-280674 | 10/1996 |
| JP | 2001-87263 | 4/2001 |

OTHER PUBLICATIONS

European Search Report, dated Oct. 2, 2008.

* cited by examiner

ULTRASOUND DIAGNOSTIC DEVICE

TECHNICAL FIELD

The present invention relates to an ultrasound diagnostic device used in the medical field.

BACKGROUND ART

As conventional ultrasound diagnostic devices, those described in JP2001-087263A and JPH08(1996)-280674A are known.

In general, ultrasound diagnostic devices employ modes called the B-mode, the M-mode, the Doppler mode (hereinafter referred to as D-mode) and the color or two-dimensional Doppler mode (hereinafter referred to as C-mode) alone or in combination. At this time, a transmission power is controlled so that a surface temperature of a portion of an ultrasound generation means contacting with a living body and an acoustic power from the ultrasound generation means to a living body do not exceed predetermined levels. Further, the transmission is conducted with a frequency, an amplitude and a wave number of a driving waveform that are determined for each mode. Thus, for a driving waveform that is different for each mode, a transmission power is controlled appropriately to have a predetermined value without excess and deficiency.

FIG. 7 is a block diagram showing an exemplary configuration of a conventional ultrasound diagnostic device. In FIG. 7, the conventional ultrasound diagnostic device is composed of: an ultrasound generation means 71; a waveform generation means 72; a mode control unit 75; a waveform control unit 74 and a voltage-variable power supply unit 73. Herein, the ultrasound generation means 71 transmits ultrasound. The waveform generation means 72 generates a single pulse or a burst pulse to drive the ultrasound generation means 71. The mode control unit 75 generates mode information concerning the mode of transmission. The waveform control unit 74 controls an amplitude and a wave number of a driving waveform that is generated by the waveform generation means 72 based on the mode information from the mode control unit 75, and controls the amplitude by using a power supply voltage. The voltage-variable power supply unit 73 determines the amplitude of the driving waveform that is generated by the waveform generation means 72.

Herein, as the voltage-variable power supply unit 73 of the ultrasound diagnostic device, a power supply ready for a high voltage exceeding several tens to hundreds volts is necessary and in order to allow for a change in voltage between the respective modes, a quick response at several tens μ-seconds is required. For those reasons, a quick-response circuit is employed, switching among a plurality of power supplies that generate different voltages is performed, or a plurality of waveform generation means with different output levels is provided in parallel with each other so as to choose a proper one for each mode.

In the above-stated conventional ultrasound diagnostic device, however, since a plurality of power supplies and a high-speed power supply should be used, the power supply unit is increased in size, which causes the problems of an increase in cost and size of the device and moreover deterioration of the reliability.

DISCLOSURE OF THE INVENTION

In view of the above-stated problems, it is an object of the present invention to provide a small ultrasound diagnostic device at a low cost that enables the appropriate control with a single power supply unit so as to give a predetermined transmission power to a driving waveform different for each mode without excess or deficiency and without affecting properties of the driving waveform.

In order to fulfill the above-stated object, a first aspect of the ultrasound diagnostic device according to the present invention includes: an ultrasound generation unit that transmits ultrasound; a waveform generation unit that generates a single pulse or a burst pulse whose duty factor is variable so as to drive the ultrasound generation unit; and a power supply unit that determines an amplitude of a driving waveform generated by the waveform generation unit.

In order to fulfill the above-stated object, a second aspect of the ultrasound diagnostic device according to the present invention includes: an ultrasound generation unit that transmits ultrasound; a waveform generation unit that generates a single pulse or a burst pulse whose duty factor is variable in units of a time that is a period corresponding to a frequency outside a frequency band of the ultrasound generation unit so as to drive the ultrasound generation unit; and a power supply unit that determines an amplitude of a driving waveform generated by the waveform generation unit.

With the above-stated configurations, an acoustic power of the ultrasound transmitted from the ultrasound generation unit can be controlled without making the transmission amplitude variable, and an unnecessary increase of harmonics due to the change of duty factor can be suppressed. Therefore, an increase of the acoustic power and an increase of a surface temperature, which result from the transmission of unnecessary energy, can be suppressed as well.

In order to fulfill the above-stated object, a third aspect of the ultrasound diagnostic device according to the present invention includes: an ultrasound generation unit that transmits ultrasound; a waveform generation unit that generates a single pulse or a burst pulse whose duty factor is variable in units of a time that is a period corresponding to a frequency outside a frequency band of the ultrasound generation unit so as to drive the ultrasound generation unit; a mode control unit that generates mode information for every transmission; a waveform control unit that sets a pulse width, a wave number and a duty factor of a driving waveform generated by the waveform generation unit based on the mode information from the mode control unit; and a power supply unit that determines an amplitude of the driving waveform generated by the waveform generation unit.

With this configuration, an acoustic power of the ultrasound transmitted from the ultrasound generation unit can be controlled without making a transmission amplitude variable for each mode, thus suppressing an increase in unnecessary second harmonics resulting from a change of duty factor. Thereby, as well as the suppression of an increase in acoustic power and an increase in surface temperature resulting from the transmission of unnecessary energy, the driving amplitude of driving waveforms for the respective modes can be made uniform, whereby it is unnecessary to incorporate a plurality of and quick-response power supply units.

Further, according to a fourth aspect of the ultrasound diagnostic device of the present invention: in the first through the third aspects, the waveform generation unit includes: a fundamental waveform generation unit that generates the single pulse or the burst pulse; a modulated wave generation unit that generates a continuous rectangular wave whose duty factor is variable during a time period while the fundamental waveform generation unit generates pulses; and a multiplication unit that multiplies a waveform output from the fundamental waveform generation unit by a waveform output from the modulated wave generation unit so as to set a duty factor of a driving waveform for the ultrasound generation unit.

With this configuration, the multiplication unit multiplies a single pulse or a burst pulse generated by the fundamental waveform generation unit and a continuous rectangular wave with a variable duty factor that is generated by the modulated wave generation unit. Thus, a driving waveform with a variable duty factor can be generated easily by simply adding a modulated wave generation unit and a multiplication unit to an existing fundamental waveform generation unit without the use of a complicated logic circuit.

BEST MODE FOR CARRYING OUT THE INVENTION

The following describes preferred embodiments of the present invention, with reference to the drawings.

Embodiment 1

Figure 1:
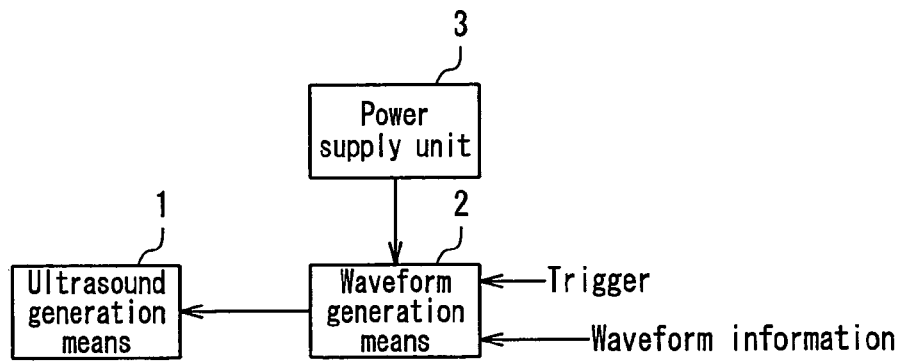
FIG. 1 is a block diagram showing one exemplary configuration of an ultrasound diagnostic device according to Embodiment 1 of the present invention.

FIG. 1 is a block diagram showing one exemplary configuration of an ultrasound diagnostic device according to Embodiment 1 of the present invention.

In FIG. 1, the ultrasound diagnostic device of the present embodiment is composed of: an ultrasound generation means 1; a waveform generation means 2 and a single power supply unit 3. The ultrasound generation means 1 transmits ultrasound. The waveform generation means 2 generates a single pulse or a burst pulse so as to drive the ultrasound generation means 1, in which a duty factor of a single pulse or a burst pulse is variable in the time units of a period corresponding to a frequency outside the frequency band of the frequency characteristics (T) of the ultrasound generation means 1 in FIG. 2 (higher-frequency side than (T)). The power supply unit 3 determines the amplitude of a driving waveform that is generated by the waveform generation means 2.

The waveform generation means 2 drives the ultrasound generation means 1 in response to a trigger input therein. The power supply unit 3 applies a constant voltage to the waveform generation means 2. The amplitude of the driving waveform generated by the waveform generation means 2 is linked to a voltage from the power supply unit 3. The waveform generation means 2 varies a duty factor of the driving waveform, whereby the power of the ultrasound can be varied as described later.

Figure 2:
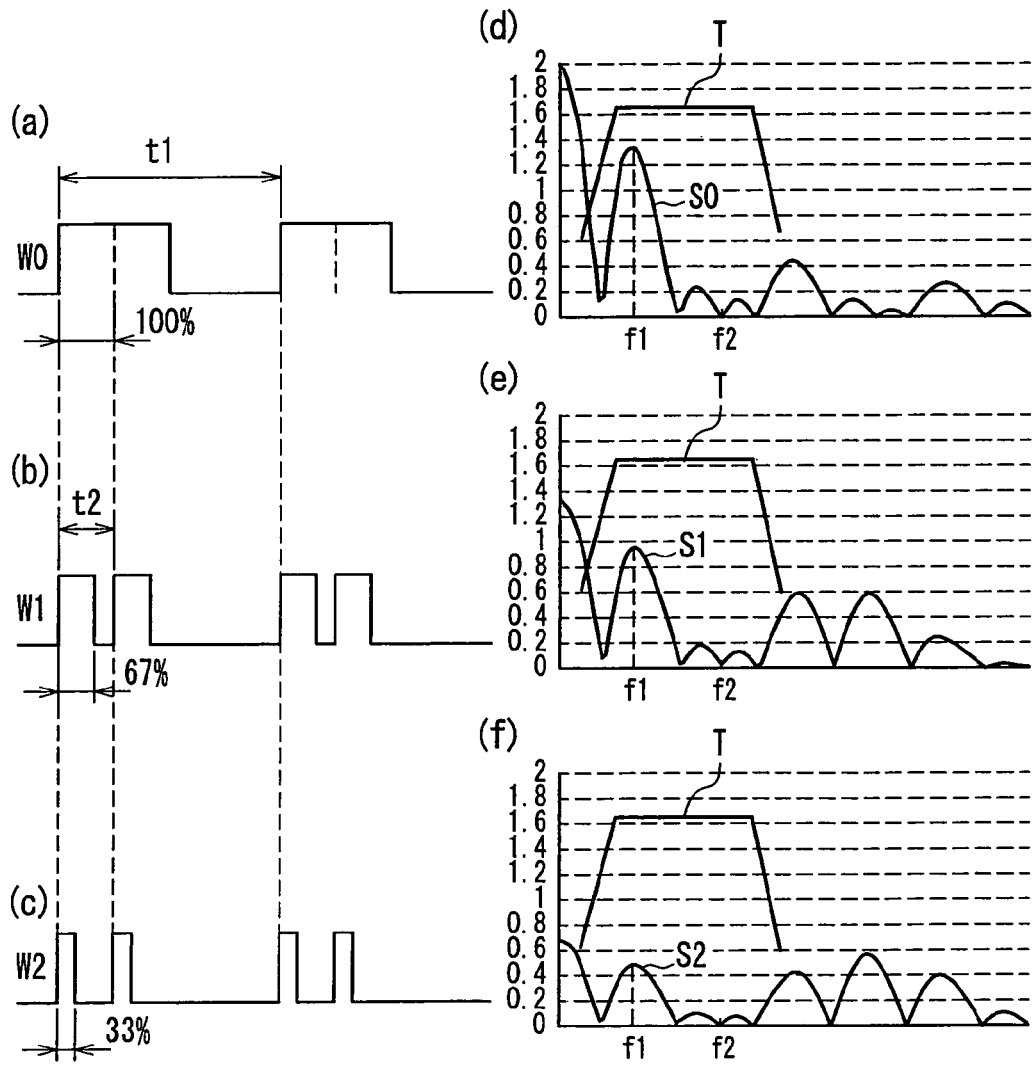
FIG. 2 shows a relationship among a driving waveform generated by a waveform generation means, frequency spectrum thereof and frequency characteristics of an ultrasound generation means in Embodiment 1 of the present invention.

FIG. 2 shows a relationship among a driving waveform generated by the waveform generation means 2, frequency spectrum thereof and frequency characteristics of the ultrasound generation means 1.

In FIG. 2, waveforms W0, W1 and W2 are driving waveforms generated by the waveform generation means 2, which have duty factors of 100%, 67% and 33%, respectively (the same holds true for other frequencies). Curves S0, S1 and S2 represent the frequency spectrum distribution corresponding to the waveforms W0, W1 and W2, respectively. T represents the frequency characteristics of the ultrasound generation means 1.

In W0 to W2, a period t1 is determined in accordance with a frequency of ultrasound to be transmitted, and in the waveform W0 with a duty factor of 100% (i.e., not varied), the spectrum of the driving waveform (S0 at f1) is within the frequency band (T) of the ultrasound generation means 1. A period t2 is for letting the duty factor variable, which is set to have a frequency outside the frequency band of the ultrasound generation means 1 (higher-frequency side than T).

As is evident from FIG. 2, in the frequency spectra S0 to S2 corresponding to the driving waveforms W0 to W2, the component with a peak at the frequency of f1 is a dominant frequency component that is converted into ultrasound by the ultrasound generation means 1. By setting the duty factors appropriately, the dominant frequency component f1 can be increased or decreased (made higher or lower of the spectrum distribution at f1 in FIG. 2) while fixing the voltage of the power supply unit 3.

It should be noted here that a feature of the present embodiment resides in that the reciprocal of the variable period t2 of the duty factor is set as a frequency outside the frequency band of the ultrasound generation means 1, which corresponds to the way by pulse width modulation in general. Effects of the present embodiment can be obtained even from an extremely short variable period t2. However, in that case, the time control accuracy for realizing such a variable period t2 would be increased, thus making the implementation thereof difficult. For that reason, in order to make it easier to obtain the effect of the present embodiment, appropriate t1/t2 is an even number and 4 or more (see the fact that the spectrum at f2 in FIGS. 2(b) and (e) is not increased).

Figure 3:
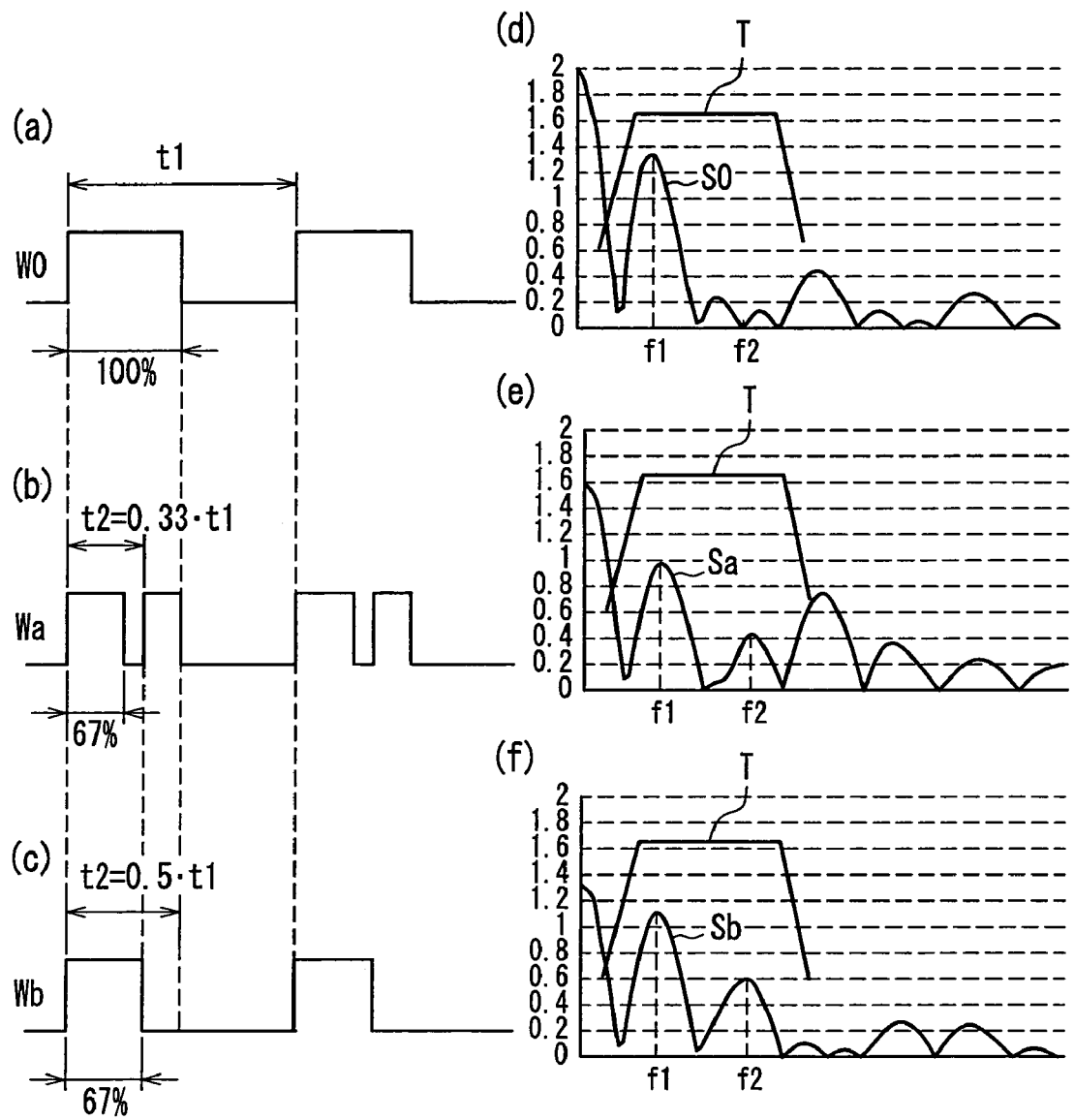
FIG. 3 shows a relationship among a driving waveform generated by the waveform generation means, frequency spectrum thereof and frequency characteristics of the ultrasound generation means in Embodiment 1 of the present invention in the case where a variable period t2 is set within a frequency band of the ultrasound generation means.

FIG. 3 shows an inappropriate example, having a variable period deviating from that of the appropriate duty factor shown in FIG. 2. Unlike FIG. 2, FIG. 3 shows the case where the variable period t2 is set within the frequency band of the ultrasound generation means 1. Similarly to FIG. 2, FIG. 3 shows a relationship among a driving waveform generated by the waveform generation means 2, frequency spectrum thereof and frequency characteristics of the ultrasound generation means 1.

In FIG. 3, W0, Wa and Wb represent driving waveforms generated by the waveform generation means 2, which show the examples of duty factors of 100%, 67% and 33%, respectively. Curves S0, Sa and Sb represent the frequency spectrum distribution corresponding to the waveforms W0, Wa and Wb, respectively. T represents the frequency characteristics of the ultrasound generation means 1.

When the variable period t2 of the duty is set at a frequency within the frequency band of the ultrasound generation means 1, a harmonic component f2 appears within the frequency band of the ultrasound generation means 1, and even if the duty factor is decreased, driving due to the harmonic component f2 is carried out (the spectrum at f2 in FIGS. 3(e) and (f) is increased). Thus, the effect of suppressing an acoustic power and heat generation cannot be obtained.

As stated above, according to the present embodiment, an acoustic power of ultrasound transmitted from the ultrasound generation means can be controlled without varying the transmission amplitude, and an unnecessary increase of harmonics due to the change of duty factor can be suppressed. Therefore, an increase of the acoustic power and an increase of a surface temperature, which result from the transmission of unnecessary energy, can be suppressed as well.

Embodiment 2

Figure 4:
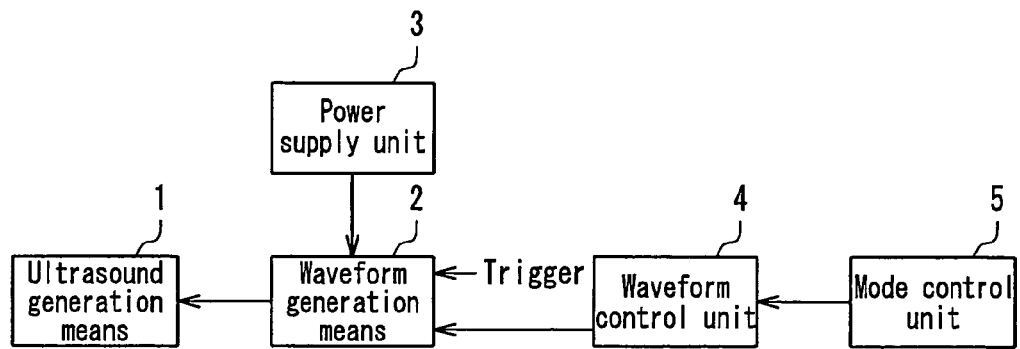
FIG. 4 is a block diagram showing one exemplary configuration of an ultrasound diagnostic device according to Embodiment 2 of the present invention.

FIG. 4 is a block diagram showing one exemplary configuration of an ultrasound diagnostic device according to Embodiment 2 of the present invention.

In FIG. 4, a duty factor of a driving waveform from a waveform generation means 2 is made variable so as to control an acoustic power, which is similar to Embodiment 1. In the present embodiment, in accordance with current mode information that is generated by a mode control unit 5, a waveform control unit 4 further determines a driving waveform, which is to be generated by the waveform generation means 2, so as to correspond to waveform information that is determined for each mode corresponding to the mode information at present.

Due to a given upper limit of the acoustic power, in the B-mode and the M-mode, which emphasize resolution in general, a peak of the amplitude should be increased with a reduced wave number. In the Doppler (including two-dimensional Doppler) mode, sensitivity is emphasized, and therefore the wave number should be increased. As a method for controlling an acoustic power within a limited range when a wave number is different for each mode, a power supply voltage may be made variable. In ultrasound diagnostic devices, however, in a shorter case, acoustic pulses are transmitted at intervals of several tens μs, and in the case where plural modes operate concurrently, acoustic pulses for different modes should be transmitted alternatively or in order. As a result, the power supply voltage should be switched in a short time.

In the present embodiment, however, the power supply voltage is not variable for each mode. The mode control unit 5 generates information concerning the mode of transmission at present, and the waveform control unit 4 holds a period t1, a period t2, a wave number and a duty factor corresponding to the mode. Therefore, the waveform information corresponding to the present mode is sent to the waveform generation means 2, so as to drive the ultrasound generation means 1.

As stated above, according to the present embodiment, an acoustic power of ultrasound transmitted from the ultrasound generation means can be controlled without making a transmission amplitude variable for each mode, thus suppressing an increase in unnecessary second harmonics resulting from a change of duty factor. Thereby, as well as the suppression of an increase in acoustic power and an increase in surface temperature, resulting from the transmission of unnecessary energy, the driving amplitude of driving waveforms for the respective modes can be made uniform, whereby it is unnecessary to incorporate a plurality of and quick-response power supply units.

Embodiment 3

Figure 5:
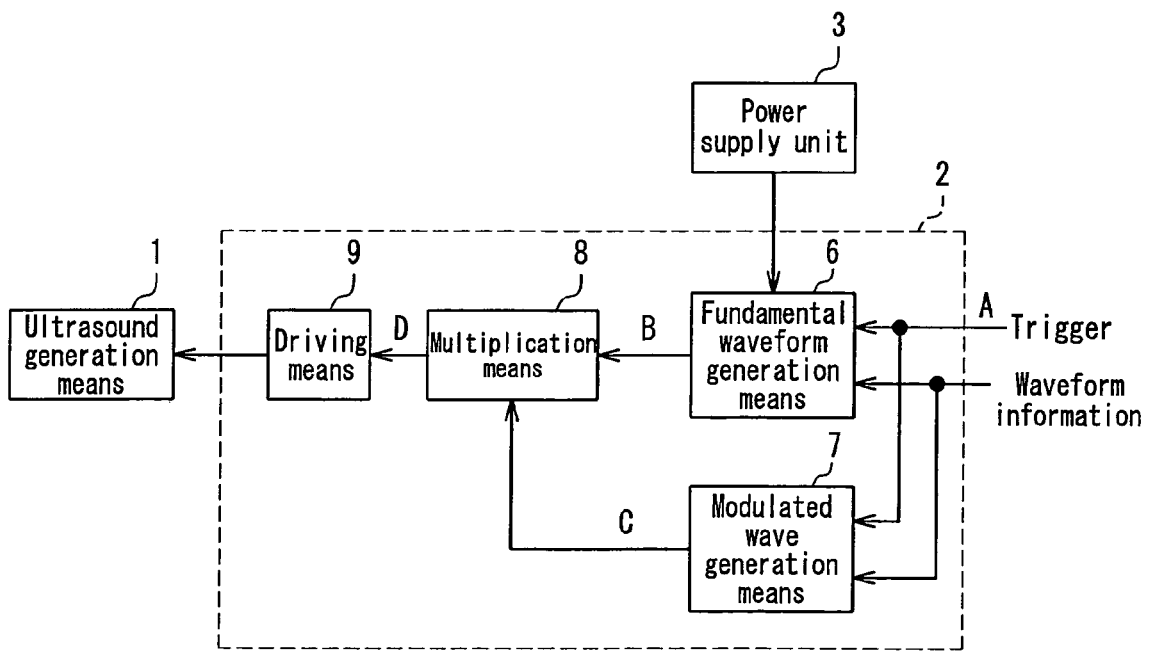
FIG. 5 is a block diagram showing an exemplary internal configuration of a waveform generation means in an ultrasound diagnostic device according to Embodiment 3 of the present invention.
Figure 6:
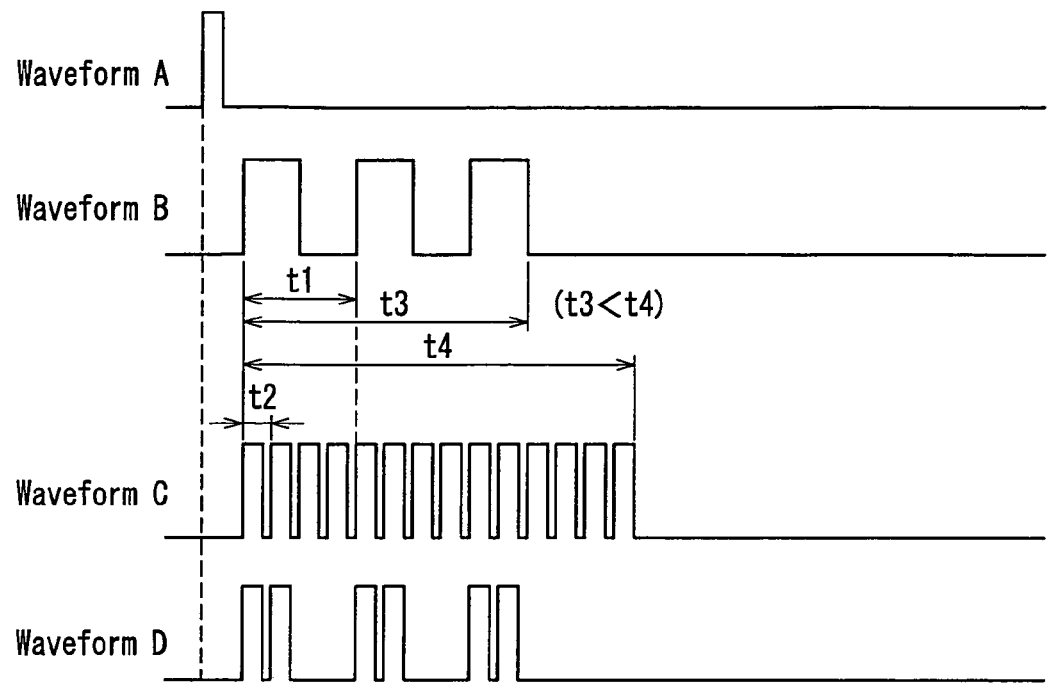
FIG. 6 is a waveform chart of signals at the respective portions in FIG. 5.
Figure 7:
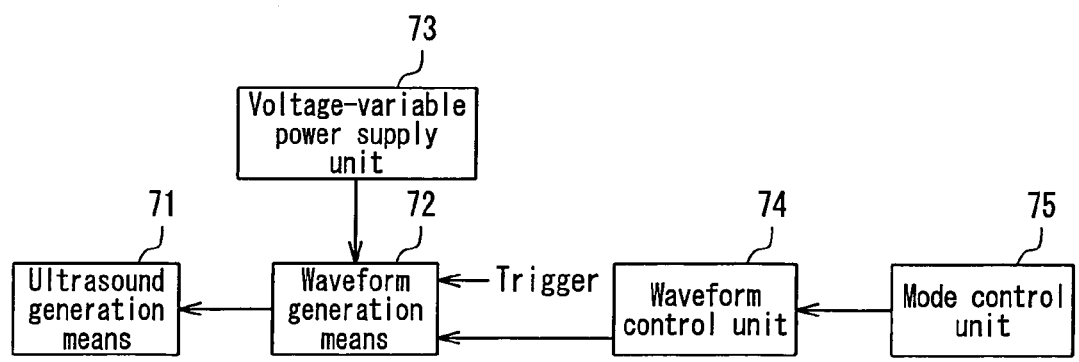
FIG. 7 is a block diagram showing an exemplary configuration of a conventional ultrasound diagnostic device.

FIG. 5 is a block diagram mainly showing an exemplary internal configuration of a waveform generation means 2 in an ultrasound diagnostic device according to Embodiment 3 of the present invention. The waveform generation means 2 shown in FIG. 5 may be applied to Embodiment 1 and Embodiment 2. FIG. 6 is a waveform chart of signals at the respective portions in FIG. 5.

In FIG. 5, the waveform generation means 2 is composed of a fundamental wave generation means 6, a modulated wave generation means 7, a multiplication means 8 and a driving means 9.

The following describes the operation of the thus configured waveform generation means 2, with reference to FIG. 5 and FIG. 6.

The fundamental waveform generation means 6 and the modulated wave generation means 7 are triggered by a trigger waveform A, and the waveforms output from both means are in synchronization with each other. The fundamental waveform generation means 6 generates a driving waveform B that is for driving an ultrasound generation means 1, where the driving waveform B is determined by waveform information containing a period t1 and a wave number. The modulated wave generation means 7 outputs a waveform C whose duty factor has been controlled, and then the multiplication means 8 multiplies the waveform C by the waveform B, so as to make a duty factor of a waveform D variable. The waveform C is determined by a period t2 and a duty factor, and has a length including the entire time period of the waveform B (t3<t4). Herein, in the case of a digital circuit, the multiplication means 8 may be a circuit such as XOR circuit and AND circuit.

The fundamental waveform generation means 6 in the present embodiment may be one included in a conventional ultrasound diagnostic device, which performs the deflection and convergence of ultrasound beams, as well as the generation of waveforms for driving the ultrasound generation means 1. Although FIG. 5 shows a complicated configuration in which the driving means 9 is included for driving the ultrasound generation means 1 at a high voltage, the present embodiment can be implemented by simply adding the modulated wave generation means 7 and the multiplication means 8 to a conventional ultrasound diagnostic device.

As stated above, according to the present embodiment, the multiplication means multiplies a single pulse or a burst pulse generated by the fundamental waveform generation means and a continuous rectangular wave with a variable duty factor that is generated by the modulated wave generation means. Thus, a driving waveform with a variable duty factor can be generated easily by simply adding a modulated wave generation means and a multiplication means to an existing fundamental waveform generation means without the use of a complicated logic circuit.

It should be noted here that although all of the above Embodiments 1 to 3 exemplify and describe a unipolar rectangular pulse waveform, the present invention is not limited to this and is applicable to a bipolar rectangular pulse with positive and negative polarities as well.

As described above, according to the present invention, the following special effect can be obtained: a small ultrasound diagnostic device can be provided at a low cost that enables the appropriate control by a single power supply unit so as to give a predetermined transmission power to a driving waveform different for each mode without excess or deficiency and without affecting properties of the driving waveform.

The invention claimed is:

1. An ultrasound diagnostic device, comprising:

an ultrasound generation means that transmits ultrasound;

a waveform generation means that generates a driving waveform comprising a single pulse or burst pulses in response to a trigger input, so as to drive the ultrasound generation means;

a mode control unit that generates mode information for every transmission;

a waveform control unit that sets a pulse width, a wave number and a duty factor of the driving waveform generated by the waveform generation means based on the mode information from the mode control unit so as to correspond to waveform information that is determined for each mode corresponding to the mode information; and a power supply unit that determines an amplitude of the driving waveform generated by the waveform generation means, wherein the single pulse or each pulse of the burst pulses of the driving waveform comprises subsidiary pulses, and a duty factor of the subsidiary pulses is less than 100% of the single pulse or each pulse of the burst pulses and variable in a time period corresponding to a frequency band above a frequency band of the ultrasound generation means.

2. The ultrasound diagnostic device according to claim 1, wherein the waveform generation means comprises: a fundamental waveform generation means that generates the single pulse or the burst pulse; a modulated wave generation means that generates a continuous rectangular wave whose duty factor is variable during a time period while the fundamental waveform generation means generates pulses; and a multiplication means that multiplies a waveform output from the fundamental waveform generation means by a waveform output from the modulated wave generation means so as to set a duty factor of a driving waveform for the ultrasound generation means.

* * * * *